United States Patent [19]

Sasaki et al.

[11] Patent Number: 4,762,863
[45] Date of Patent: Aug. 9, 1988

[54] PHOTOPOLYMERIZABLE DENTAL COMPOSITION CONTAINING A HEXAFUNCTIONAL URETHANE METHACRYLATE BASED ON ISOCYANURIC ACID

[75] Inventors: Isao Sasaki, Saeki; Nobuhiro Mukai, Hiroshima; Hitoshi Ige, Ohtake, all of Japan

[73] Assignee: Mitsubishi Rayon Co., Ltd., Tokyo, Japan

[21] Appl. No.: 84,096

[22] Filed: Aug. 11, 1987

[30] Foreign Application Priority Data

Mar. 30, 1987 [JP] Japan .................... 62-077186

[51] Int. Cl.$^4$ .................................... C08J 6/08
[52] U.S. Cl. .................................... 522/11; 523/116
[58] Field of Search .................. 522/11; 523/116

[56] References Cited

U.S. PATENT DOCUMENTS 4,440,878  4/1984  Kawahara et al. ............... 523/116

*Primary Examiner*—Harold D. Anderson
*Assistant Examiner*—Frederick Krass
*Attorney, Agent, or Firm*—Cushman, Darby & Cushman

[57] ABSTRACT

Disclosed is a photopolymerizable dental composition consisting essentially of (A) a composite filler obtained by non-catalytically polymerizing a carboxylic acid monomer with a vinyl monomer in a polymerization system having an inorganic compound dispersed therein; (B) a monomer mixture composed of 2,2-bis[4-(methacryloxyethoxy)phenyl]propane, at least one hexafunctional urethane methacrylate having an isocyanuric acid skeleton, and an ethylenic vinyl monomer diluent; and (C) a photopolymerization initiator. The composite resin obtained by curing this dental composition has high mechanical strength and good water resistance.

8 Claims, No Drawings

PHOTOPOLYMERIZABLE DENTAL COMPOSITION CONTAINING A HEXAFUNCTIONAL URETHANE METHACRYLATE BASED ON ISOCYANURIC ACID

BACKGROUND OF THE INVENTION

1. Field of the Invention

This invention relates to a dental prosthetic composition containing a high proportion of a comproshite filler as an inorganic filler. More particularly, it relates to a photopolymerizable dental prosthetic composition which can readily be polymerized and cured by exposure to visible light to give a cured product having high mechanical properties and good water resistance.

2. Description of the Prior Art

It is important that dental prosthetic materials have not only good physical properties such as mechanical strength, abrasion resistance, water resistance and adhesion properties, but also excellent aesthetic properties such as transparency and polishability so as to bear greater resemblance to natural teeth. In order to provide satisfactory substitutes for amalgam, many attempts have been made to develop so-called composite resins formed by blending an inorganic filler with an organic resin in order to improve the aforesaid properties.

Such composite resins consist of three main components: (1) an inorganic filler, (2) an olefinically unsaturated compound and (3) a polymerization initiator.

However, when an inorganic filler is simply blended with an organic resin, the resulting composite resin has poor interfacial affinity (i.e., poor compatibility and adhesion properties between the inorganic filler and the organic resin) and fails to exhibit satisfactorily high performance. Thus, in order to overcome this shortcoming, there have been proposed dental materials containing a filler which have undergone a surface treatment, for example, with a silane coupling agent. However, the surface treatment with a silane coupling agent has the great disadvantage that its applicability is limited because it is only effective for glassy fillers having silanol groups in the surface. Moreover, since the silonxane bonds so formed are subject to hydrolysis, the resulting treated filler has poor water resistance. Accordingly, in the case of quartz-based fillers commonly used in dental prosthetic compositions chiefly for the purpose of imparting thereto high hardness and desirable aesthetic properties, it is difficult to achieve a desired interfacial reinforcing effect. Further, such treated fillers are also disadvantageous from a clinical point of view because, during long-term use in the wet oral cavity, their poor water resistance causes a reduction in mechanical strength with time.

In addition, much research has been made into the monomers constituting the aforesaid organic resin. For example, it has been found that bisphenol A-derived multifunctional monomers, as typified by bisphenol A diglycidyl dimethacrylate (hereinafter referred to as Bis-GMA), can provide composite resins exhibiting a low degree of shrinkage on polymerization, and that hydrophobic monomers such as 2,2-bis[4-methacryloxyethoxy)phenyl]propane (hereinafter referred to as Bis-MEPP) can provide composite resins having excellent water resistance. However, Bis-GMA is disadvantageous in that, since it has a hydroxyl group in the molecule, the resulting cured product exhibits high water absorption and hence poor water resistance. On the other hand, Bis-MEPP has low curability and fails to give a satisfactorily high cross-linking density, so that the resulting cured product has poor mechanical strength. Further, attempts have been made to overcome these disadvantages by the combined use of Bis-GMA and Bis-MEPP, but a mere combination thereof has failed to provide a composite resin having excellent properties. In the existing state of the art, therefore, a very wide range of monomer compositions must be examined to determine the monomer composition most suitable for the intended purpose.

SUMMARY OF THE INVENTION

It is an object of the present invention to provide a photopolymerizable dental composition which can give a cured product having high mechanical strength and good water resistance.

It is another object of the present invention to provide a photopolymerizable dental composition in which the aforesaid excellent properties can be achieved by using any desired inorganic filler.

According to the present invention, there is provided a photopolymerizable dental composition consisting essentially of (A) a composite filler obtained by polymerizing at least one carboxylic monomer of the general formula

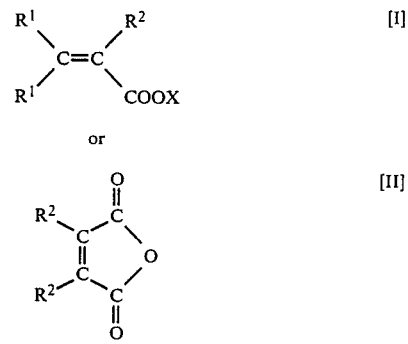

where each $R^1$ independently represents a hydrogen atom, an alkyl group of 1 to 15 carbon atoms, a —COOX group, a halogen atom, or a phenyl group or its derivative, each $R^2$ independently represents a hydrogen atom, an alkyl group of 1 to 15 carbon atoms, a halogen atom, or a phenyl group or its derivative, and X represents a hydrogen atom, an ammonium group or an alkali metal atom, with at least one radicalpolymerizable vinyl monomer in a polymerization system having an inorganic compound dispersed therein;

(B) a monomer mixture composed of (i) 2,2-bis[4-(methacryloxyethoxy)phenyl]propane, (ii) at least one hexafunctional urethane (meth)acrylate of the general formula

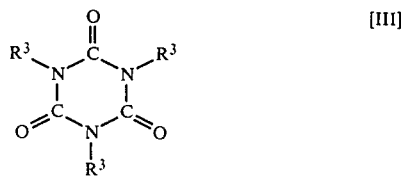

where each $R^3$ represents

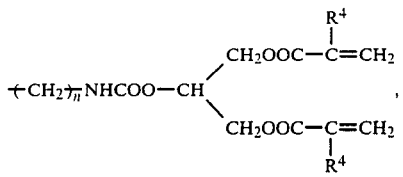

n is a whole number of 1 to 10, and each $R^4$ independently represents a hydrogen atom or a methyl group, and (iii) an ethylenic vinyl monomer diluent; and
(C) a photopolymerization initiator.

DETAILED DESCRIPTION OF THE PREFERRED EMBODIMENTS

The composite filler (A) constituting the composition of the present invention is obtained by non-catalytically polymerizing a carboxylic monomer with one or more other polymerizable vinyl monomers in a polymerization system having an inorganic compound dispersed therein. No particular limitation is placed on the method for preparing the composite filler (A). According to one preferred method, the composite filler (A) is prepared by carrying out an aqueous heterogeneous polymerization reaction under temperature conditions which do not cause thermal polymerization to occur. More specifically, a vinyl monomer and an inorganic compound are suspended and dispersed in an aqueous medium, and a carboxylic monomer is added to this suspension. Then, the resulting reaction mixture is stirred under the aforesaid temperature conditions for a predetermined period of time.

The specific carboxylic monomer of the above general formula [I] or [II], which is used for the preparation of the composite filler (A), should indispensably have a carboxyl group as an active site for imparting polymerizability thereto, and a double bond as an active site for establishing a firm bond between the formed polymer and the inorganic compound. There may be used any of the compounds having a chemical structure containing those functional groups. Specific examples of useful carboxylic monomers include acrylic acid, methacrylic acid, crotonic acid, tiglic acid, cinnamic acid, maleic anhydride and citraconic anhydride. Among these, acrylic acid, methacrylic acid, crotonic acid and maleic anhydride are preferred because of their high polymerizability.

The inorganic compound used for the preparation of the composite filler (A) is selected from among metals of groups I, II, III and IV of the periodic table; transition metals; oxides, hydroxides, chlorides, sulfates, sulfites, carbonates, phosphates and silicates of such metals; and mixtures and complexes of such compounds. Among these, barium sulfate, barium fluoride, silicon dioxide, aluminum oxide, titanium oxide, quartz powder, glass powder, glass beads, glass fibers, glass fillers containing a barium, lead or strontium salt, silica gel, zirconium oxides and tin oxides are preferred because they are highly effective in activating vinyl monomers and forming a firm bond with polymers. It is one of the outstanding features of the present invention that inorganic compounds resistant to ordinary coupling treatments can also be used and, moreover, inorganic compounds having any desired particle shape and size may be chosen.

The vinyl monomer used in preparing the composite filler (A) of the present invention can be any of conventional radicalpolymerizable vinyl monomers. Specific examples thereof include alkyl esters of (meth)acrylic acid, such as methyl methacrylate and butyl acrylate; aromatic vinyl monomers such as styrene and α-methylstyrene; vinyl cyanide monomers such as acrylonitrile and methacrylonitrile; and such monomers as are useful as ethylenic vinyl monomer diluents in the monomer mixture (B) and will be enumerated later. Any desired vinyl monomer may be chosen according to the intended purpose.

In preparing the composite filler (A), the carboxylic monomer is used in an amount of about 0.05 to 100% by weight, preferably 0.1 to 50% by weight and more preferably 0.5 to 30% by weight, based on the combined weight of the inorganic compound and the vinyl monomer. In most cases, it is preferable to increase the amount of the carboxylic monomer in proportion to that of the vinyl monomer. The weight ratio of the vinyl monomer (or vinyl monomer mixture) to the inorganic compound can vary widely. It usually ranges from about 500:1 to about 1:5 and preferably from about 50:1 to about 1:1. Where the polymerization is carried out in an aqueous medium, the amount of water should be about 0.01 to about several hundred times, preferably about 0.1 to about 10 times, the combined weight of the inorganic compound and the vinyl monomer. Usually, the reaction is carried out under an atmosphere of an inert gas (such as nitrogen or the like) at a temperature of about 10° to 100° C. and preferably 20° to 80° C. Although the particular reaction temperature may be suitably determined according to the type of the vinyl monomer used, it is important to carry out the reaction at a temperature which can suppress thermal polymerization to a minimal degree. If the reaction is carried out at an elevated temperature which allows a marked degree of thermal polymerization to occur, the resulting composite filler will fail to form a firm bond of the inorganic compound and the organic polymer and will fail to exhibit a sufficient degree of uniformity. The reaction time ranges from 30 minutes to about 15 hours. The resulting composite filler (A) can be dried in a temperature range of about 10° to 300° C. and preferably about 50° to 200° C. The interaction between the surfaces of the inorganic compound and the organic polymer formed in the above-described manner is believed to surpass that of simple adsorption or physical adhesion caused by, for example, van der Waals force. This is obvious from the fact that, when the composite filler (A) is subjected to an extraction treatment with a good solvent for the formed vinyl polymer, a large portion of the vinyl polymer remains unextracted.

In the above-described composite filler (A), the vinyl polymer is firmly bonded with the inorganic compound, so that the inorganic compound and organic polymer present in the resulting composite resin have good compatibility. Accordingly, the dental composition of the present invention can be prepared by choosing and using any inorganic compounds as required for dental compositions according to the intended purpose.

It is essential that the monomer mixture (B) used in the composition of the present invention contain Bis-MEPP and a hexafunctional urethane (meth)acrylate of the general formula [III].

Thus, it has unexpectedly been found that the combined use of the aforesaid two monomers in the composition of the present invention makes it possible to obtain a composite resin having high mechanical strength (due to a high crosslinking density) and good water resistance.

Among the monomers represented by the general formula [III], the hexafunctional urethane acrylate in which n is 6 and two $R^4$ radicals are hydrogen and methyl (hereinafter referred to as U-6HA), and the hexafunctional urethane methacrylate in which n is 6 and two $R^4$ radicals are both methyl (hereinafter referred to as U-6H) are preferred because of their good curability. Of these monomers, U-6HA is the most preferred.

In the composition of the present invention, no particular limitation is placed on the proportions of Bis-MEPP, the hexafunctional urethane (meth)acrylate and the ethylenic vinyl monomer diluent constituting the monomer mixture (B). However, based on the workability of the resulting photopolymerizable composition, it is preferable to use those monomers in such proportions that the resulting photopolymerizable composition will have a viscosity of 1,000 to 500,000 poises (at 25° C.). Bis-MEPP and the hexafunctional urethane (meth)acrylate are preferably used in amounts of 40 to 70% by weight and 10 to 40% by weight, respectively, based on the total amount of the monomer mixture (B). Moreover, from the viewpoint of water resistance and mechanical strength, the weight ratio of the hexafunctional urethane (meth)acrylate to Bis-MEPP should preferably range from about 0.2:1 to about 0.5:1.

The ethylenic vinyl monomer diluent used in the composition of the present invention can be any conventional monomer that is known to be suitable for use in dental composite resins. Specific examples thereof include alkanediol (meth)acrylates such as triethylene glycol dimethacrylate and 1,6-hexamethylene glycol dimethacrylate; polyalkylene glycol di(meth)acrylates such as triethylene glycol dimethacrylate and tetraethylene glycol di(meth)acrylate; trimethylolpropane tri(meth)acrylate; glycidyl (meth)acrylate; alkyl esters of (meth)acrylic acid such as methyl methacrylate and butyl acrylate; aromatic hydrocarbons such as styrene, α-methylstyrene; and vinyl cyanide compounds such as acrylonitrile, methacrylonitrile. In the composition of the present invention, the radical-polymerizable vinyl monomer used for the preparation of the composite filler (A) may be the same as that used in the monomer mixture (B).

The amounts of the composite filler (A) and the monomer mixture (B) may be determined according to the type of the inorganic compound used in the composite filler (A), the type of the monomer mixture (B), the purpose of use of the resulting composition, and other factors. However, the composite filler (A) and the monomer mixture (B) are preferably used in amounts of 20 to 90 parts by weight and 10 to 80 parts by weight, respectively, provided that the combined amount of (A) and (B) is 100 parts by weight.

No particular limitation is placed on the type of the photopolymerization initiator (C) used in the composition of the present invention. However, in consideration of its use in the oral cavity and the possible harm caused by ultraviolet light, it is desirable to use a photopolymerization initiator sensitive not only to near-ultraviolet light but also to visible light in the wavelength range of 400 to 800 nm. Moreover, it is desirable from a clinical point of view that the composition of the present invention cure within 30 seconds or so. On the basis of the above-described considerations, preferred examples of the photopolymerization initiator (C) include α-diketone compounds such as camphorquinone, benzil and diacetyl as well as mixtures thereof.

Such α-diketone compounds can be used in combination with reducing agents such as dimethylaminoethyl methacrylate and alkyl esters of 4-(N,N-dimethylamino)benzoic acid. Especially preferred reducing agents are $C_{5-10}$ alkyl esters of 4-(N,N-dimethylamino)benzoic acid including, for example, isoamyl 4-(N,N-dimethylamino)benzoate. In the composition of the present invention, it is preferable from the viewpoint of curability to use, as the photopolymerization initiator, a mixture of an α-diketone compound as defined above and a $C_{5-10}$ alkyl ester of 4-(N,N-dimethylamino)benzoic acid.

The amount of the photopolymerization initiator may be determined considering the curability and storage stability of the resulting composition. For example, if the photopolymerization initiator comprises a mixture of an α-diketone compound and an alkyl ester of 4-(N,N-dimethylamino)benzoic acid, the α-diketone compound is usually used in an amount of 0.01 to 15% by weight, preferably 0.05 to 5% by weight and more preferably 0.1 to 2% by weight, based on the monomer mixture (B), and the alkyl ester of 4-(N,N dimethylamino)benzoic acid is usually used in an amount of 0.05 to 15% by weight based on the monomer mixture (B).

In order to modify its viscosity, transparency, hiding power and other properties, the composition of the present invention may contain additional fillers according to the need. Fillers useful for this purpose include metals of the groups I, II, III and IV of the periodic table; transition metals; oxides, hydroxides, chlorides, sulfates, sulfites, carbonates, phosphates and silicates of such metals; and mixtures and complexes of such compounds; and the like. Among others, silicon dioxide, quartz powder, aluminum oxide, barium sulfate, titanium oxide, talc, glass powder, glass beads, glass fibers, glass fillers containing a barium, lead or strontium salt, silica gel, colloidal silica, carbon fibers, zirconium oxides, tin oxides and other ceramic powders are preferred. The above-enumerated fillers may be used in any of various forms including untreated fillers, fillers having undergone a surface treatment with, for example, a silane coupling agent, and inorganic fillers physically coated with a polymer.

The amount of the aforesaid fillers may vary according to the purpose of use of the resulting photopolymerizable dental composition. However, they are usually used in an amount of 0.1 to $1 \times 10^3$% by weight, preferably 0.5 to $5 \times 10^2$% by weight and 1 to $1 \times 10^2$% by weight, based on the aforesaid monomer mixture (B), so as to give a pasty composition.

If desired, the composition of the present invention may further contain colorants, polymerization inhibitors (such as hydroquinone, methoxybenzophenone, methylphenol and hydroquinone monomethyl ether), antioxidants, ultraviolet light absorbers (such as benzophenone), pigments (such as iron oxides and titanium oxides) and similar additives.

The present invention is further illustrated by the following examples; however, it is to be understood that the present invention is not limited thereto. In these examples, all parts are by weight.

In the following examples, certain properties of the resulting compositions were evaluated according to the procedures described hereinbelow.

(1) Compression strength and water resistance

Each photopolymerizable dental composition was charged into a stainless steel mold having an inner diameter of 4 mm and a height of 6 mm. Then, cover glasses having a thickness of about 0.1 mm were brought into contact with the top and bottom surfaces of the composition. Using a visible light irradiator (Optilux; manufactured by Minnesota Mining and Manufacturing Co.) positioned so that its projection aperture was 1 mm from the cover glass, the top and bottom surfaces of the composition were irradiated for 30 seconds each. The resulting cured product was stored in water at 37° C. for 24 hours and then tested for compression strength. Moreover, its water resistance was evaluated by storing the cured product in water at 37° C. for a week and then measuring its compression strength. Compression strength was measured at a crosshead speed of 1.0 mm/min with a Tensiolon (Model IS-500; manufactured by Shimadzu Corp.).

(2) Water absorption

Using a stainless steel mold having an inner diameter of 20 mm and a height of 1 mm, each photopolymerizable composition was cured in the same manner as described above. The water absorption of the resulting cured product was evaluated by storing it in water at 37° C. for a week and then measuring its weight increase per unit surface area.

EXAMPLE 1

Into a 500-ml four-necked separable flask fitted with a cooling coil, a nitrogen inlet tube, a stirring rod and a thermocouple for measuring the internal temperature were charged 50 g of finely powdered quartz (prepared from A-2 quartz powder obtained from Tatsumori K.K. and pulverized to an average particle diameter of 1–2 $\mu$m) and 50 g of finely powdered barium glass (prepared from #7724 barium glass obtained from Corning Glass Works and pulverized to an average particle diameter of 1–2 $\mu$m) as inorganic compounds. These inorganic compounds were suspended and dispersed in 300 ml of deionized water and nitrogen gas was passed through the resulting suspension for 30 minutes. Then, 3.0 g of methyl methacrylate as a vinyl monomer was added, with vigorous stirring, to the suspension under an atmosphere of nitrogen. Then, the flask was immersed in a warm-water bath to warm the suspension to 70° C. After it was confirmed that the added monomer remained in a uniformly dispersed state, 0.5 g of acrylic acid as a carboxylic monomer was slowly added to the suspension and polymerization reaction was carried out at 70° C. for 8 hours.

After completion of the reaction, the product was separated by filtration under reduced pressure, washed thoroughly with deionized water, and then dried in hot air at 100° C. to remove any moisture therefrom. Thus, there was obtained about 100 g of a composite filler. This composite filler had a polymer content of 2.5% as determined by the calcination method. When the composite filler was subjected to a Soxhlet extraction test in which it was extracted with hot benzene for 50 hours, its polymer content after extraction treatment was found to be 2.0%. This revealed that, in the composite filler obtained in the above-described manner, most of the polymer was very firmly grafted with the surfaces of the quartz powder and barium glass powder. When composite fillers were prepared by using the same polymerization system containing 100 g of either quartz powder or barium glass powder alone, their polymer contents were found to be almost equal to that of the composite filler obtained by using the aforesaid mixture. Thus, it was presumed that the two types of inorganic compounds present in the aforesaid composite filler were evenly grafted with the polymer.

90 g of the aforesaid composite filler based on a mixture of quartz powder and barium glass powder was blended with 10 g of Aerosil R-972 (hydrophobic amorphous silica; manufactured by Degussa Inc.). To 70 parts of this filler blend was added a monomer mixture (B) composed of 18 parts of Bis-MEPP, 6 parts of U-6HA (manufactured by Shin-Nakamura Kagaku K.K.) and 6 parts of triethylene glycol dimethacrylate (hereinafter referred to as 3G). Finally, as photopolymerization initiators (C), camphorquinone and isoamyl 4-(N,N-dimethylamino)benzoate (hereinafter referred to as DABA) were added thereto in amounts of 0.4% by weight and 2.0% by weight, respectively, based on the monomer mixture (B). The photopolymerizable composition so prepared was then cured and various properties of the resulting cured product were evaluated. The results are shown in Table 1.

EXAMPLE 2

A composite filler was prepared in the same manner as described in Example 1, except that the acrylic acid used as a carboxylic monomer was replaced by maleic anhydride. Then, this composite filler was blended with the aforesaid amount of Aerosil R-972. Using this filler blend, a photopolymerizable composition was prepared according to the same formulation as employed in Example 1. Then, the photopolymerizable composition was evaluated in the same manner as described in Example 1, and the results are shown in Table 1. The composite filler prepared in the above-described manner had a polymer content similar to that observed in Example 1.

COMPARATIVE EXAMPLES 1 AND 2

For purposes of comparison, photopolymerizable compositions were prepared according to the same formulation as employed in Example 1, except that the composite filler of the present invention was replaced by conventional fillers. More specifically, there was used a silane-treated filler blend obtained by treating a mixture of 50 g of quartz powder and 50 g of barium glass powder with 3% of a silane coupling agent. [KBM-#503 (3-methacryloyloxypropyl trimethoxy silane); manufactured by Shin-Etsu Silicone Co.] and then blending 90 g of the resulting silane-treated fillers with 10 g of Aerosil R-972 (Comparative Example 1), and an untreated filler blend obtained by blending 45 g of untreated quartz powder, 45 g of untreated barium glass powder and 10 g of Aerosil R-972 (Comparative Example 2). The photopolymerizable compositions so prepared were evaluated in the same manner as described in Example 1, and the results are shown in Table 1.

TABLE 1

| | Evaluation of properties | | |
|---|---|---|---|
| | Compression strength (kg/cm$^2$) | Water absorption (mg/cm$^2$) | Water resistance (kg/cm$^2$) |
| Example 1 | 3300 | 0.20 | 3300 |
| Example 2 | 3280 | 0.21 | 3270 |
| Comparative Example 1 | 2900 | 0.43 | 2500 |
| Comparative | 2200 | 0.35 | 2000 |

TABLE 1-continued

| | Evaluation of properties | | |
|---|---|---|---|
| | Compression strength (kg/cm$^2$) | Water absorption (mg/cm$^2$) | Water resistance (kg/cm$^2$) |
| Example 2 | | | |

It is evident from the data of Table 1 that the dental materials containing a composite filler (A) in accordance with the present invention (Examples 1 and 2) provided cured products having more excellent mechanical strength and water resistance, compared with those containing conventional silane-treated fillers (Comparative Example 1) or untreated fillers (Comparative Example 2).

It was also found that the composite filler (A) used in accordance with the present invention exhibited very good wettability with the monomer mixture (B), thus making it easy to form a composite resin. Moreover, the resulting cured product presented a markedly attractive appearance, compared with those of Comparative Examples 1 and 2.

EXAMPLE 3

A composite filler was prepared by carrying out an aqueous heterogeneous polymerization reaction in the same manner as described in Example 1, except that 100 g of aluminum oxide powder (reagent grade) was used as the inorganic compound. This composite filler had a polymer content of 2.5%, and its polymer content after extraction treatment was 2.0%. To 30 parts of the aforesaid composite filler based on aluminum oxide powder was added a monomer mixture (B) composed of 42 parts of Bis-MEPP, 14 parts of U-6HA and 14 parts of 3G. Finally, as photopolymerization initiators (C), camphorquinone and DABA were added thereto in amounts of 0.4% by weight and 2.0% by weight, respectively, based on the monomer mixture (B). The photopolymerizable composition so prepared was then cured and various properties of the resulting cured product were evaluated. The results are shown in Table 2.

COMPARATIVE EXAMPLES 3 AND 4

Photopolymerizable compositions were prepared according to the same formulation as employed in Example 3, except that the composite filler of Example 3 was replaced by conventional fillers. More specifically, there was used a silane-treated filler comprising aluminum oxide powder treated with 3% of a silane coupling agent (Comparative Example 3), and an untreated filler comprising untreated aluminum oxide powder (Comparative Example 4). The photopolymerizable compositions so prepared were evaluated in the same manner as described in Example 3, and the results are shown in Table 2.

TABLE 2

| | Evaluation of properties | |
|---|---|---|
| | Compression strength (kg/cm$^2$) | Water absorption (mg/cm$^2$) |
| Example 3 | 1020 | 0.25 |
| Comparative Example 3 | 390 | 0.59 |
| Comparative Example 4 | 410 | 0.45 |

It is evident from the data of Table 2 that, similar to the results shown in Table 1, the dental composition containing a composite filler in accordance with the present invention provided a cured product having more excellent properties, as compared with those containing conventional silane-treated fillers or untreated fillers.

EXAMPLES 4–8 AND COMPARATIVE EXAMPLES 5–9

Dental compositions were prepared according to the same formulation as employed in Example 1, except that each of the monomer mixtures (B) shown in Table 3 was used. Then, various properties of their cured products were evaluated in the same manner as described in Example 1. The results are shown in Table 3.

It is evident from the data of Table 3 that cured products having excellent mechanical strength and water resistance and hence suitable for use as a dental material can be obtained by using a mixture of specific monomers as the monomer mixture (B).

TABLE 3

| | Formulation of photopolymerizable dental composition | | | | | | | | Evaluation of properties | |
|---|---|---|---|---|---|---|---|---|---|---|
| | Filler of Example 1 (parts) | Monomer mixture (B) (parts) | | | | | Photopolymerization initiator (C) (parts)*[3] | | Compression strength (kg/cm$^2$) | Water absorption (mg/cm$^2$) |
| | | Bis-MEPP | Bis-GMA*[1] | U-6HA | U-6H*[2] | 3G | Camphorquinone | DABA | | |
| Example 4 | 70 | 18 | — | — | 6 | 6 | 0.4 | 2.0 | 3280 | 0.19 |
| Example 5 | " | 20 | — | 4 | — | " | " | " | 3300 | 0.19 |
| Example 6 | " | 16 | — | — | 8 | " | " | " | 3320 | 0.21 |
| Example 7 | " | 11 | — | 13 | — | " | " | " | 3200 | 0.31 |
| Example 8 | " | 22 | — | 2 | — | " | " | " | 3000 | 0.19 |
| Comparative Example 5 | " | 24 | — | — | — | " | " | " | 2700 | 0.19 |
| Comparative Example 6 | " | — | 24 | — | — | " | " | " | 3200 | 0.54 |
| Comparative Example 7 | " | 12 | 12 | — | — | " | " | " | 2840 | 0.43 |
| Comparative Example 8 | " | — | 18 | 6 | — | " | " | " | 3340 | 0.46 |
| Comparative Example 9 | " | — | 18 | — | 6 | " | " | " | 3360 | 0.45 |

*[1]Bisphenol A diglycidyl dimethacrylate.
*[2]Manufactured by Shin-Nakamura Kagaku K.K.
*[3]The amount added per 100 parts of the monomer mixture (B).

EXAMPLES 9 AND 10

Dental compositions were prepared according to the same formulation as employed in Example 1, except that each of the reducing agents shown in Table 4 was used. Then, various properties of their cured products were evaluated in the same manner as described in Example 1. The results are shown in Table 4.

COMPARATIVE EXAMPLES 10 AND 11

Dental compositions were prepared according to the same formulation as employed in Comparative Example 1, except that each of the reducing agents shown in Table 4 was used. Then, various properties of their cured products were evaluated in the same manner as described in Example 1. The results are shown in Table 4.

TABLE 4

| | Formulation of photopolymerizable dental composition | | | | | | | Evaluation of properties | |
|---|---|---|---|---|---|---|---|---|---|
| | Filler | | Monomer mixture (B) | | | Photopolymerization initiator (C) (parts)*1 | | Compression | Water |
| | | | Amount | | | | Reducing agent | strength | absorption |
| | Type | (parts) | Bis-MEPP | U-6HA | 3G | Camphorquinone | Type  Amount | (kg/cm$^2$) | (mg/cm$^2$) |
| Example 9 | Example 1 | 70 | 18 | 6 | 6 | 0.4 | X*2  2.0 | 3000 | 0.27 |
| Example 10 | Example 1 | " | " | " | " | " | Y*3  " | 3100 | 0.25 |
| Comparative Example 10 | Comparative Example 1 | " | " | " | " | " | X  " | 2800 | 0.46 |
| Comparative Example 11 | Comparative Example 1 | " | " | " | " | " | Y  " | 2900 | 0.42 |

*1The amount added per 100 parts of the monomer mixture (B).
*2X: Ethyl 4-(N,N—dimethylamino)benzoate.
*3Y: Dimethylaminoethyl methacrylate.

What is claimed is:

1. A photopolymerizable dental composition consisting essentially of
   (A) a composite filler obtained by polymerizing at least one carboxylic monomer of the general formula

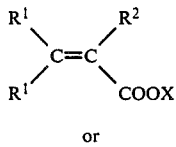

or

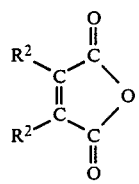

where each $R^1$ independently represents a hydrogen atom, an alkyl group of 1 to 15 carbon atoms, a —COOX group, a halogen atom, or a phenyl group or its derivative, each $R^2$ independently represents a hydrogen atom, an alkyl group of 1 to 15 carbon atoms, a halogen atom, or a phenyl group or its derivative, and X represents a hydrogen atom, an ammonium group or an alkali metal atom, with at least one radicalpolymerizable vinyl monomer in a polymerization system having an inorganic compound dispersed therein;
   (B) a monomer mixture consisting of (i) 2,2-bis[4-(methacryloxyethoxy)phenyl]propane, (ii) at least one hexafunctional urethane (meth)acrylate of the general formula

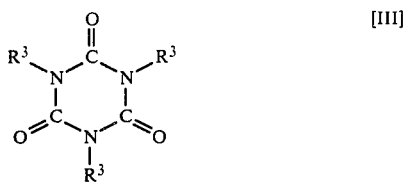

where each $R^3$ represents

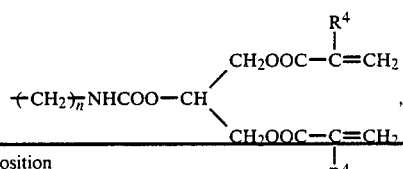

n is a whole number of 1 to 10, and each $R^4$ independently represents a hydrogen atom or a methyl group, and (iii) an ethylenic vinyl monomer diluent; and
   (C) a photopolymerization initiator.

2. A photopolymerizable dental composition as claimed in claim 1 wherein the carboxylic monomer constituting the composite filler (A) is at least one compound selected from the group consisting of acrylic acid, methacrylic acid, crotonic acid and maleic anhydride.

3. A photopolymerizable dental composition as claimed in claim 1 wherein the inorganic compound constituting the composite filler (A) is at least one compound selected from barium sulfate, barium fluoride, silicon dioxide, aluminum oxide, titanium oxide, quartz powder, glass powder, glass beads, glass fibers, glass fillers containing a barium, lead or strontium salt, silica gel, zirconium oxides and tin oxides.

4. A photopolymerizable dental composition as claimed in claim 1 wherein the photopolymerization initiator (C) is a mixture of an α-diketone compound and a reducing agent.

5. A photopolymerizable dental composition as claimed in claim 4 wherein the α-diketone compound is at least one compound selected from the group consisting of camphorquinone, benzil and diacetyl.

6. A photopolymerizable dental composition as claimed in claim 4 wherein the reducing agent is a $C_{5-10}$ alkyl ester of 4-(N,N-dimethylamino)benzoic acid.

7. A photopolymerizable dental composition as claimed in claim 1 consisting of 20 to 90 parts by weight of the composite filler (A), 10 to 80 parts by weight of the momoner mixture (B), and 0.001 to 12 parts by weight of the photopolymerzation initiator (C), provided that the combined amount of (A) and (B) is 100 parts by weight.

8. A photopolymerizable dental composition consisting essentially of (A) a composite filler obtained by polymerizing at least one carboxylic monomer of the general formula

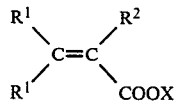
[I]

where each $R^1$ independently represents a hydrogen atom, an alkyl group of 1 to 15 carbon atoms, a —COOX group, a halogen atom, or a phenyl group or its derivative, each $R^2$ independently represents a hydrogen atom, an alkyl group of 1 to 15 carbon atoms, a halogen atom, or a phenyl group or its derivative, and X represents a hydrogen atom, an ammonium group or an alkali metal atom, with at least one radicalpolymerizable vinyl monomer in a polymerization system having an inorganic compound dispersed therein;

(B) a monomer mixture composed of (i) 2,2-bis[4-(methacryloxyethoxy)phenyl]propane, (ii) at least one hexafunctional urethane (meth)acrylate of the general formula

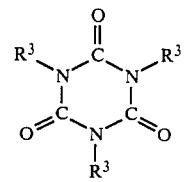
[III]

where each $R^3$ represents

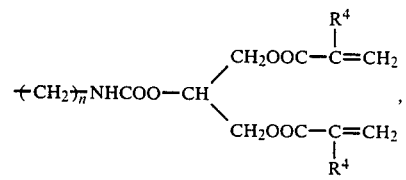

n is a whole number of 1 to 10, and each $R^4$ independently represents a hydrogen atom or a methyl group, and (iii) an ethylenic vinyl monomer diluent; and (C) a photopolymerization initiator.

* * * * *